United States Patent [19]
Hasegawa

[11] Patent Number: 5,511,103
[45] Date of Patent: Apr. 23, 1996

[54] METHOD OF X-RAY MAPPING ANALYSIS

[75] Inventor: Kiyoshi Hasegawa, Chiba, Japan

[73] Assignee: Seiko Instruments Inc., Japan

[21] Appl. No.: 325,805

[22] Filed: Oct. 19, 1994

[51] Int. Cl.$^6$ .................................................. G01N 23/223
[52] U.S. Cl. ..................... 378/44; 250/341.4; 250/492.3; 378/64; 378/208
[58] Field of Search ................................ 250/341.4, 359, 250/458.1, 492.3; 378/20, 44, 64, 209, 208

[56] References Cited

U.S. PATENT DOCUMENTS

| | | | |
|---|---|---|---|
| 4,152,723 | 5/1979 | McMahon et al. | 358/106 |
| 4,556,903 | 12/1985 | Blitchington et al. | 358/106 |
| 5,424,841 | 6/1995 | Van Gelder et al. | 356/417 |

FOREIGN PATENT DOCUMENTS 0268256  11/1990  Japan ................................ 250/458.1

*Primary Examiner*—David P. Porta
*Assistant Examiner*—David Vernon Bruce
*Attorney, Agent, or Firm*—Adams & Wilks

[57] ABSTRACT

The sample stage is scanned in a grid pattern with a feed pitch finer than the width of the primary beams, and with X-ray intensities at each point as values, primary and secondary mapping data are prepared. In order to convert the shape and size of the primary beam into a size of each of the mapping data, a beam template is prepared in which portions irradiated with primary beam being "1" and portions not irradiated being "0". The background intensity is determined as a threshold value, and at the positions where the value of the primary mapping data is below the threshold value, beam template is overlaid on the secondary mapping data. Those values in the secondary mapping data corresponding to "1" portions of the beam template are replaced with "0", and this is performed over all the measured points, thereby data closely approximating the actual boundary of the element concerned is obtained on the secondary mapping data.

3 Claims, 3 Drawing Sheets

■ : PARTS IRRADIATED BY PRIMARY BEAM (1)

□ : PARTS NOT IRRADIATED BY PRIMARY BEAM (0)

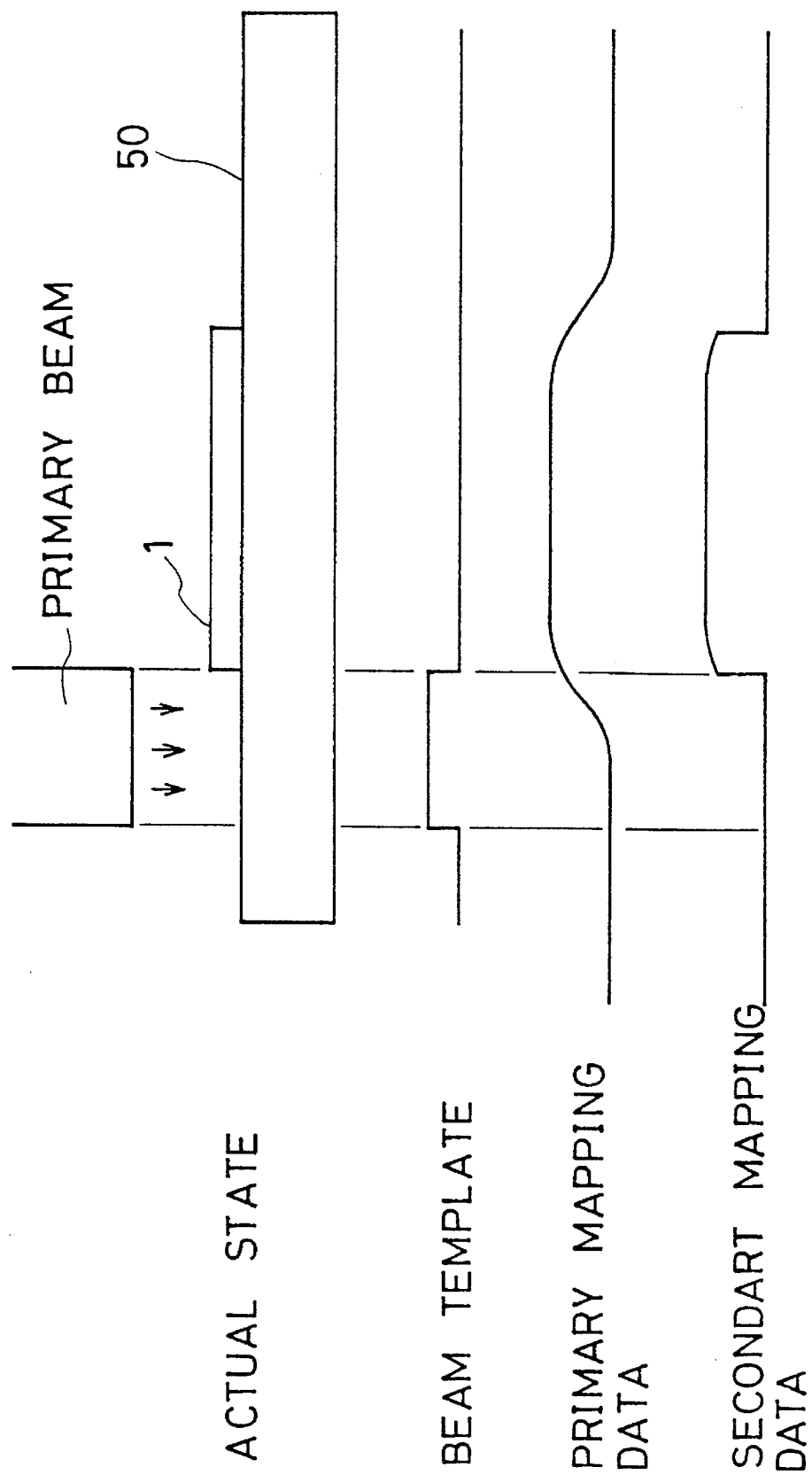

METHOD OF X-RAY MAPPING ANALYSIS

BACKGROUND OF THE INVENTION

This invention relates to X-ray mapping analysis methods which examine distribution of elements by irradiating samples with an electron beam or an X-ray beam or the like and detect the X-rays induced from the sample.

Conventionally element boundary cannot be detected in a resolution finer than the size of the primary beam, such as an electron beam and an X-ray beam, radiated to the sample to be measured. The detected result is used as mapping data as it is; mapping data is output by setting a threshold value of X-ray intensity and eliminating the data that is below the intensity threshold. However, in conventional methods, there are problems that threshold value which detects the actual element boundary line cannot be obtained as shown for X-ray intensity distribution 8 taken on section 7 in FIG. 1, and that in some conditions another boundary line is generated within the actual element boundary.

SUMMARY OF THE INVENTION

The method according to the present invention utilizes, in an X-ray mapping device capable of recognizing the shape and the size of a primary beam that allows X-rays to be excited, the steps comprising:

1. scanning the sample stage in a grid pattern with a feed pitch finer than the primary beam size and detecting X-ray intensity of the element concerned at each grid position,
2. with X-ray intensities as values, preparing a pair of identical two-dimensional arrays wherein measurement points are arranged in a matrix, and thus preparing primary and secondary mapping data,
3. converting the shape and size of the primary beam into a size of each of the mapping data and preparing a two-dimensional beam template of a rectangular form including the primary beam, in said beam template portions irradiated with the primary beam being "1", and portions not irradiated being "0",
4. determining the intensity of the background of the element concerned from the intensity distribution in the primary mapping data to use said intensity as a threshold value for detection of said element concerned, and
5. at the positions where the X-ray intensity of the primary mapping data is below threshold value, overlaying the beam template on the primary mapping data and replacing with "0" those values in the secondary mapping data that are overlaid with "1" portions of said beam template and performing the replacement over all the measured points, whereby the boundary of the element concerned is detected on the secondary mapping data in a resolution finer than the primary beam size.

In an X-ray mapping device which operates as described above, while the sample stage is moved with a feed pitch finer than the primary beam size, while the primary beam is being moved from outside the boundary of the element concerned to inside the boundary, X-rays from the element concerned can be detected, if only slightly, at the point when the edge of the primary beam is overlaid with the boundary line. At this point, the center of the primary beam has not reached the inside of the boundary and the center of the primary beam is still outside the boundary, distant from the boundary by half of the beam width. Then, if the shape and the size of the primary beam are known, the actual boundary position can be recognized. Since the primary beam shape is not always truly round, a beam template is prepared. By converting the shape and size of the primary beam into the mapping data size, a beam template is prepared to define the area irradiated with the primary beam. In the beam template, the area irradiated by the primary beam is set with the value "1" and the remaining area is set with the value "0". Portions set with "0" shows that those portions are not irradiated with the primary beam and no data is available for these positions. Therefore at the measurement positions where the X-rays of the element concerned are not detected, no element concerned exists in the portions "1" of the beam template, and accordingly mapping data in such positions that correspond to these portions can be replaced with "0".

By following the steps above, the resolution can be finer than the size of the primary beam in the detection of the boundary of the elements concerned.

BRIEF DESCRIPTION OF THE DRAWINGS

FIG. 5 is a diagram of mapping data when the sample is scanned in a one-dimensional direction.

DETAILED DESCRIPTION OF THE INVENTION

An embodiment of the present invention will now be described with reference to the drawings.

[Embodiment 1]

Figure 1:
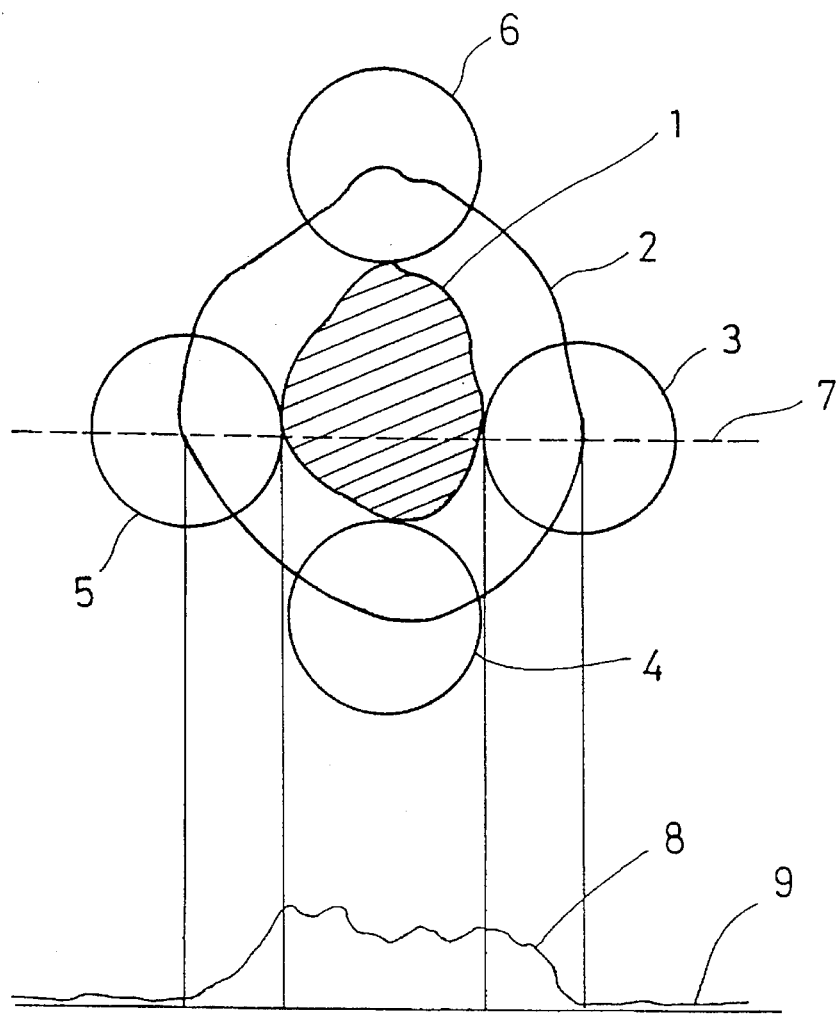
FIG. 1 is a diagram illustrating the method of increasing the horizontal resolution of the mapping data.
Figure 3:
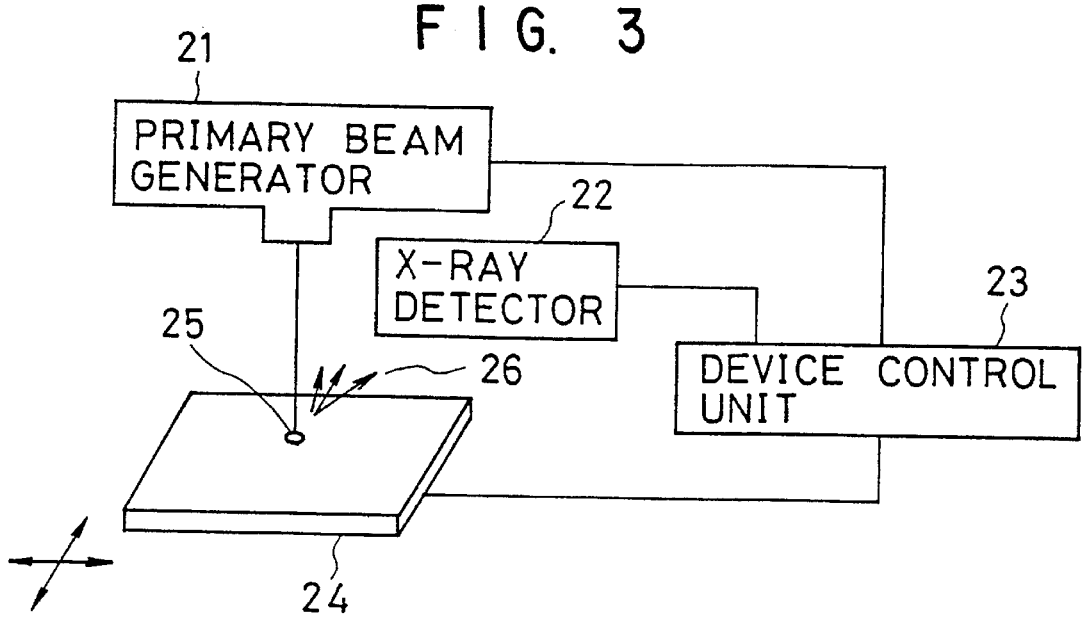
FIG. 3 is a schematic diagram of the configuration of an X-ray mapping device employed in the invention.

FIG. 3 is an example of the X-ray mapping device utilized according to the invention. A sample 25 is irradiated with a primary beam from a primary beam generator controlled by a device controller while a sample stage 24 is scanned in longitudinal and lateral axis. In FIG. 1, the sample stage is scanned in a grid pattern over the region including an element concerned 1, with primary beams 3 to 6 for which an X-ray is used, with a feed pitch finer than the primary X-ray beam width, and the X-ray intensity of the element concerned is detected at each grid position. Scanning in a grid pattern means, for example, scanning from the upper left end to the upper right end and then, after moving downward by one line, scanning from the left to the right again and repeating this for each line.

Using the X-ray intensities as values, a pair of identical two-dimensional array data is prepared as primary and secondary mapping data. Two-dimensional array data is a group of information in which position information is arranged in rows and columns and whose values are the intensities at each measurement position. An example of the data is as follows:

Data [0] [0]: Intensity in the first-from-the-left and topmost position

Data [0] [1]: Intensity in the second-from-the-left and topmost position

| Data [0] [1]: | Intensity in the second-from-the-left and topmost position |
|---|---|
| . | |
| . | |
| Data [1] [0]: | Intensity in the first-from-the-left and the second-from-the-top position |

Figure 2:
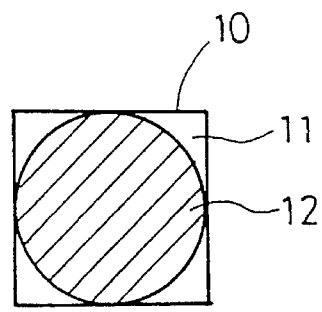
FIG. 2 is a schematic diagram of the beam template.
Figure 4:
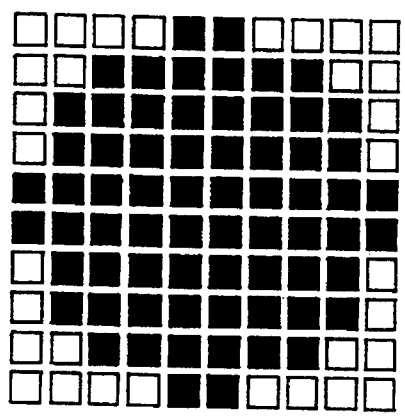
FIG. 4 is a detailed diagram of the beam template.

Data [1] [0]: Intensity in the first-from-the-left and the second-from-the-top position The shape and size of the primary beam, obtained using a photosensitive film or the like, is converted into the size of the mapping data. For this purpose, as shown in FIG. 2, a two-dimensional beam template 10 having a rectangular form including the primary beam is prepared. In the template 10, the value for the portions irradiated with primary beam 12 is set to "1", and the value for the portions not irradiated 11 is set to "0". A beam template is illustrated in detail in FIG. 4; in which the shape and size of the beam are represented with portions irradiated by the primary beam set to "1" (black) and portions not irradiated set to "0" (white). Assuming that the beam shape is truly round with 100-μm of diameter, when the element concerned has been measured with a 10-μm feed pitch both longitudinally and laterally, a mapping data comprising a 10×10 grid which is a square including a circle of 100-μm diameter is prepared and data of "1" or "0" is set to each position of the grid. The resulting grid is used as a beam template. The steps of preparing a beam template using a photosensitive film are as follows:

1. irradiate a photosensitive film with a primary beam to allow the film to be exposed.
2. draw lines of grids on the photosensitive film and recognize 1 or 0 for each grid.
3. recognize the number of grids and the size of each grid.

From the intensity distribution 8 in the primary mapping data in FIG. 1 a threshold value of the X-ray intensity for detection of the element concerned is determined. Generally background intensity 9 is used for the threshold value. At the positions where X-ray intensity of the primary mapping data is below the threshold value, the beam template is overlaid on the secondary mapping data, and data in the secondary mapping data corresponding to those portions that are overlaid with the value "1" portions of the beam template are replaced with "0". This is performed over all the measured points.

The above steps will now be explained with reference to FIG. 5, which gives an example of performing the above steps for one-dimensional data. The beam is assumed to be truly round. In FIG. 5, when measurement is performed by scanning the element concerned 1, which is put on a base material 50, from left to right, the relationship between the beam center and the detected X-ray intensity is as follows: since the primary beam is not a point, the detected X-ray intensities in the primary mapping data do not exhibit discrete change in value at the boundary between the element concerned 1 and the base material 50 as shown in the figure, therefore the boundary of the element concerned cannot be distinctly recognized; immediately before the edge of the primary beam reaches the element concerned, the detected X-ray intensity is identical with the background intensity (X-ray intensity detected when a base material is irradiated with a primary beam); since the primary beam has not reached the element concerned yet at that time, the portions corresponding to the width of the primary beam, i.e. the width of the beam template, is considered to be the background. Therefore data [0] is given to such portions of the secondary mapping data that correspond to the beam template, thereby the final secondary mapping data is provided. Following the steps above, data closely approximating the actual boundary of the element concerned 1 is obtained on the secondary mapping data.

[Embodiment 2]

Also when an electron beam is used for the primary beam of embodiment 1 to detect X-rays from a sample, the sample boundary can be recognized in a resolution finer than the size of the electron beam by following the same steps as in embodiment 1.

In the field of X-ray mapping analysis performed for electronic parts which have been increasingly miniaturized in density and size, the present invention brings about lots of advantages in examining the size of minute flaws and in measuring the dimensions. Particularly when an X-ray is used as a primary beam, focusing a primary X-ray into a beam with a diameter of under 50 μm is costly, therefore achieving higher mapping resolution has been very difficult. By using the method of the present invention, high resolution mapping image can be obtained with reduced cost.

By using the method of the present invention, in the investigation of foreign matter and in the analysis of the minute part in material segregation analysis and the like, with a beam size available at a cheaper price, distribution can be checked in a resolution finer than the beam size. Furthermore, since the beam does not need to be collimated more than needed, appropriate detection intensity is obtained, resulting in reduced time required for the measurement and reduced system cost. The invention is also effective in examining foreign matters with a complicated shape.

What is claimed is:

1. A method of X-ray mapping analysis in an X-ray mapping device comprising an excitation beam source which irradiates samples with a primary beam to excite X-rays, a controllable sample stage movable in at least longitudinal and lateral axes, an X-ray detector which detects said X-rays from said samples and a data processor which processes data, said method comprising the steps of:

scanning said sample stage in a grid pattern with a feed pitch finer than said primary beam size and detecting the X-ray intensity of the element concerned at each grid position, with said X-ray intensities as values, preparing a pair of identical two-dimensional arrays wherein measurement positions are arranged in a matrix, and thus preparing primary and secondary mapping data, converting the shape and size of said primary beam into the size of the mapping data and preparing a two-dimensional beam template of a rectangular form including the cross sectional area of said primary beam, in said beam template portions irradiated with primary beam being "1" and portions not irradiated being "0", determining the intensity of the background of said element concerned from intensity distribution of said primary mapping data to use said intensity as a threshold value for detection of said element concerned; and at the positions where said X-ray intensity of said primary mapping data is below the threshold value, overlaying said beam template on said primary mapping data and replacing with "0" those values in said secondary mapping data that are overlaid with "1" portions of said beam template and performing the replacement over all the measured points, whereby the boundary of the element concerned can be detected on the secondary mapping data in a resolution finer than the size of the primary beam.

2. A method of X-ray mapping analysis claimed in claim 1 characterized in that said primary beam is an X-ray beam.

3. A method of X-ray mapping analysis in an X-ray mapping device comprising an excitation beam source which irradiates a sample with a primary beam to excite X-rays, a controllable sample stage movable in at least longitudinal and lateral axes, an X-ray detector which detects said X-rays from said samples and a data processor which processes data, said method comprising the steps of:

measuring a shape and a size of said primary beam in advance;

scanning an element concerned of said sample in a grid pattern with a feed pitch finer than said primary beam size and detecting the X-ray intensity of said element concerned at each grid position;

finding positions where said X-ray intensity begins to become higher than said background intensity or said X-ray intensity begins to become equal to said background intensity; and obtaining information of said positions as data showing a boundary of said element concerned.

* * * * *